United States Patent [19]
Shimizu et al.

[11] Patent Number: 5,529,906
[45] Date of Patent: Jun. 25, 1996

[54] ANALYTICAL SYSTEM OR KIT FOR PHOSPHATASE

[75] Inventors: Akiko Shimizu; Akihiro Shinzaki; Tadao Suzuki; Miwa Watanabe, all of Uji, Japan

[73] Assignee: Mitsubishi Cable Industries, Ltd., Hyogo Prefecture, Japan

[21] Appl. No.: 154,354

[22] Filed: Nov. 18, 1993

[30] Foreign Application Priority Data

Nov. 18, 1992 [JP] Japan .................................. 4-308931

[51] Int. Cl.$^6$ .................. C12Q 1/42; G01N 33/53
[52] U.S. Cl. ................. 435/21; 435/4; 435/25; 435/26; 435/189; 435/190; 435/810; 435/975
[58] Field of Search .................. 435/21, 4, 25, 435/26, 189, 190, 810, 975

[56] References Cited

U.S. PATENT DOCUMENTS

| | | | |
|---|---|---|---|
| 4,490,465 | 12/1984 | Limbach et al. | 435/14 |
| 4,769,321 | 9/1988 | Self | 435/7.1 |
| 5,272,054 | 12/1993 | Switchenko et al. | 435/4 |

OTHER PUBLICATIONS

Khalmuratov et al, *Biological Abstracts*, vol. 73, No. 2, p. 914, Ref. #8882, 1981 (Ukr. Biokhim. Zh. 52(6):742–745, 1980).

Lövgren et al, *Analytica Chemica Acta*, vol. 288, pp. 227–235, 1994.

Primary Examiner—Michael G. Wityshyn
Assistant Examiner—Abdel A. Mohamed
Attorney, Agent, or Firm—Wenderoth, Lind & Ponack

[57] ABSTRACT

A system or kit for analysis of phosphatase comprising a reagent I containing NADP or NADPH as a main component, and a reagent II containing components for color-development signal amplification utilizing NAD-NADH interconversion, wherein at least one of the hydrogen donors participating in the NAD-NADH interconversion is included in reagent I, but not in reagent II, which eliminates the necessity that the reagent II is further separated into two parts. This enables the preparation of reagent II as a mixture which can be readily used and which can be preserved for a long period of time without "reagent blank" occurring. Additionally, the present kit eliminates the necessity of mixing reagents I and II immediately before actual use and thus permits periodical analysis of samples with a reagent having the same components for long time periods with reliable and uniform sensitivity.

4 Claims, 3 Drawing Sheets

ANALYTICAL SYSTEM OR KIT FOR PHOSPHATASE

FIELD OF THE INVENTION

The present invention relates to an analytical system or kit for phosphatase. More particularly, the present invention relates to a system or kit for enzymatic analysis of phosphatase utilizing a signal amplification system associated with oxidation-reduction cycling between nicotinamide adenine dinucleotide (hereinafter abbreviated as NAD) and its reduced form (hereinafter abbreviated as NADH).

BACKGROUND OF THE INVENTION

NAD, and NADH are the most popular coenzymes included in the body, and they participate in oxidation-reduction reactions of various dehydrogenases by means of reversible changes between AND and NADH which receive or give a hydrogen atom.

NAD and NADH can be detected or analyzed with a potent sensitivity in the aid of signal amplification system utilizing the enzymatic cycling between NAD and NADH. This signal amplification system is also applied extensively to phosphatase detection or analysis system in the fields of immunoassay and tissue staining. In spite of that the method of detection or analysis of NAD or NADH associated with the signal amplification system is colorimetric analysis, it is now an excellent method in the field of immunoassay, especially, in the measurement of alkaline phosphatase, since it can provide a potent detection sensitivity which is comparable to that in fluorescence technique (or fluorescent antibody technique) or color development technique [edited by Isikawa et al., Kohso Men-eki Sokuteihoh (in Japanese), the third edition, pp. 58–60, published by Igakushoin].

In the method, nicotinamide adenine dinucleotide phosphate (hereinafter abbreviated as NADP) or its reduced form (hereinafter abbreviated as NADPH) is coverted into NAD or NADH by catalytic action of phosphatase, the resultant NAD or NADH is detected by means of signal amplification system thereby presence of phosphatase if detected in a potent sensitivity.

As will be seen from the reaction diagram shown hereunder, when NADP is used as a substrate for phosphatase, for example, NAD is produced by catalytic action of phosphatase, the resultant NAD act as a coenzyme for oxidation reaction from ethanol to acetoaldehyde, in the presence of alcohol dehydrogenase (hereinafter abbreviated as ADH) and its substrate (for example, ethanol which is hereinafter abbreviated as EtOH), at this occasion NAD is reduced to NADH. The resultant NADH is oxidized to produce NAD in the presence of tetrazolium dye and its reductase (diaphorase), and at the same time terazolium dye is reduced to produce formazan as the color-development signal. Under the conditions mentioned above, the oxidation-reduction reaction between NAD and NADH is repeated to thereby gradually increase the signal intensity. (C. H. Self et al., Clinica Chimica Acta, Vol 148, pp. 119–124, 1985).

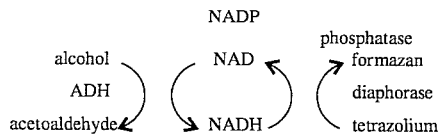

In the reaction system described, the enzyme participating in the reduction reaction of NAD to NADH must be the one which recognize NAD but does not recognize NADP, i.e. which is activated only by NAD but is not activated by NADP. Usually ADH is used in view of its potent specificity to NAD.

As will be seen from the reaction diagram shown hereunder, when NADPH is used as a substrate for phosphatase, a color development signal is generated and amplified in the same manner (principle) as described with respect to NADP in the above. In this case, it is necessary to use an enzyme participating in oxidation reaction of NADH to NAD must be the one which solely recognize NADH but do not recognize NADPH, and usually NADH-depending (or NADH-specific) diaphorase is used (F. J. Dhahir et al., Clinical Chemistry, Vol. 38 (2), pp. 227–232, 1992).

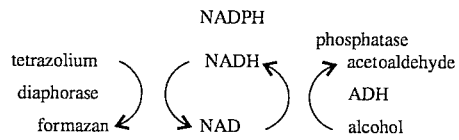

In measurement of phosphatase utilizing signal amplification system of NAD or NADH, a first reagent participating in catalytic reaction of phosphatase and a second reagent participating in signal amplification system are utilized. That is, the first reagent includes NADP or NADPH, which is the substrate for phosphatase, as the main component, and the second reagent includes enzymes for the enzymatic cycling of NAD or NADH and for enhancement of the signal amplification (for example, ADH and diaphorase) and their substrates (for example, alcohol and tetrazolium) as the main components.

The second reagent which participate in signal amplification, however, tends to show non-specific color development (hereinafter, this phenomenon is occasionally called a reagent blank) of tetrazolium dye, when all the components of the second reagent are preserved in a mixture. For this reason, it is common that the second reagent is further separated into two parts or compositions in preservation, and this necessitates to mixing them immediately before actual use.

SUMMARY OF THE INVENTION

It is an object of the present invention to provide a novel or improved system or kit for analysis of phosphatase which reagent consists of a first and a second reagents to be mixed in use wherein a second reagent participating in signal amplification is prepared as a single mixture or composition which is ready to use and which last out long period preservation without occurrence of a reagent blank.

The present invention provides a system or kit, for analysis of phosphatase, which is characterized in that said reagent consists of a Reagent I comprising NADP or NADPH, which are substrates for phosphatase, as the component and a Reagent II comprising components for color-developmenmt signal amplification utilizing NAD-NADH interconversion, wherein at least one of hydrogen donors participating in NAD-NADH interconversion is included in the Reagent I but not in the Reagent II.

According to the present invention, a system or kit for analysis of phosphatase consisting of two Reagents I and II, wherein the Reagent II which participates in signal amplification can be prepared as a mixture without necessitating to prepare it in two parts or compositions. This makes it possible to preserve Reagent II, which is heretofore necessary to separate into two parts or compositions in preservation, for a long period in a state enabling to use without a troublesome job for mixing the two parts immediately before its actual use. This enables to make periodical analysis of samples with a reagent having the same components for a long period of time and to assure reliable analysis with uniform or stable sensitivity.

BRIEF DESCRIPTION OF THE DRAWING

In FIGS. 1 and 2, ( - ● - ) denote Example 1 of the present invention wherein Reagent I contains EtOH and ( - ○ - ) denote Control 1 (conventional reagent) wherein Reagent II contains EtOH. In FIGS. 3 and 4, ( - ▲ - ) denote Example 2 of the present invention wherein Reagent I contains diaphorase and ( - △ - ) denote Control 2 wherein Reagent II contains diaphorase. In FIGS. 5 and 6, ( - ■ - ) denote Example 3 of the present invention wherein Reagent I contains both of alanine and diaphorase and ( - □ - ) denote Control 3 wherein Reagent II contains both of alanine and diaphorase.

DETAILED DESCRIPTION OF THE INVENTION

Figure 1:
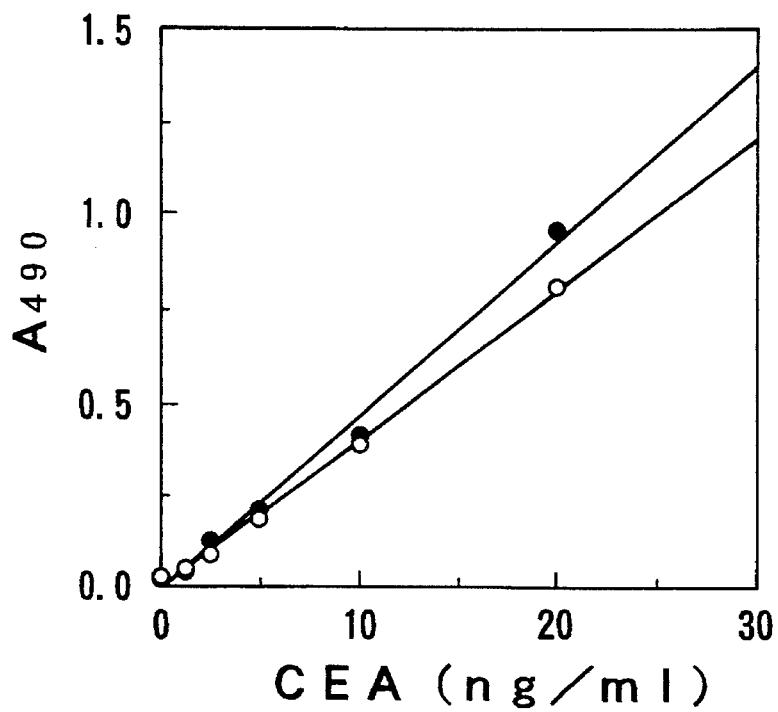
FIGS. 1, 3 and 5 show the relationships between concentration and absorbance ($A_{490}$) of carcinoembryonic antigen (hereinafter abbreviated as CEA)

The system or kit for analysis of phosphatase of the present invention consists of Reagent I and II to be mixed in use, the former participates in catalytic reaction of phosphatase and the latter participates in signal amplification reaction.

According to the present invention, Reagent I includes NADP or NADPH and one of hydrogen donors (substrate of dehydrogenase and reductase to tetrazolium dye) which participate in signal amplification reaction, and Reagent II includes the remaining components which participate in signal amplification reaction (dehydrogenase, tetrazolium, surfactant and the like) other than the hydrogen donor included in Reagent I.

When detection or measurement of phosphatase is made utilizing the analytical reagent of the present invention, Reagents I and II are initially mixed to prepare a reagent for analysis of phosphatase, a sample including phosphatase is mixed to the resultant mixture, then the resultant mixture is subjected to colorimetric analysis to determine possible change in absorbance of the resultant mixture due to the change in concentration of formazan which is produced by reduction of tetrazolium dye. The colorimetric analysis can be made by rate assay in which changes in absorbance is periodically measured, or by end point assay in which the enzymatic cycling is performed for a predetermined period, then terminated by adding acid thereto, and finally absorbance is measured. In either methods, commercially available spectrophotometers can be used for measurement of absorbance.

NADP or NADPH to be used in the analytical reagent of the present invention must be the one which do not include any components which act on the enzyme participating in signal amplification reaction. A typical concentration range of NADP or NADPH in the reagent is 0.1–100 mM, preferably 1–10 mM.

Dehydrogenase to be used in the analytical reagent of the present invention includes amino acid dehydrogenase (hereinafter abbreviated as AADH), AdH and the like having a potent specificity to NAD or NADH. For example, AADH may include alanine dehydrogenase (hereinafter abbreviated as AlaDH), leucine dehydrogenase (hereinafter abbreviated as LeuDH), glatamate dehydrogenase and the like. Any ADH, for example, those originated from baker's yeast, a microorganism belonging to genus of Zymomonus and the like, can be used, and their origin is not limited. Typical concentration range of these dehydrogenases is 0.01–1000 units/ml, preferably 0.1–100 units/mi. One unit of dehydrogenase means the quantity of enzymes which can oxidize 1 μmol of corresponding substrate per minute at pH 9.0 and 30° C.

When AADH is used as dehydrogenase, a specific amino acid corresponding to a specific AADH should be used. Alcohol such as ethanol is used as a substrate for ADH. Typical concentration range of substrates for dehydrogenases in the analytical reagent is 1–1000 mM, preferably 10–100 mM. Any buffer solution having buffer action within neutral pH range, for example, phosphoric acid buffer, triethanol buffer and the like can be used. A typical pH range of the buffer is 5.0–10.0, preferably 7.0–9.0. A typical concentration range of the buffer in the analytical reagent is 10–1000 mM, preferably 50–500 mM.

Examples of tetrazolium dye include 2-(p-nitrophenyl)-3-(p-iodophenyl)- 5-phenyltetrazolium chloride (hereinafter abbreviated as INF), 3,3'-( 3,3'-dimethoxy-4,4'-diphenylene) bis (2-(p-nitrophenyl)-5-phenyltetrazolium chloride), 2-(4', 5'-dimethyl-2'-thyazolyl-3,5-diphenyltetrazolium bromide and the like. A typical concentration range of tetrazolium dye in the analytical reagent is 0.1–10 mM, preferably 0.5–2 mM.

As to diaphorase, there is no specific limitation on its origin, however, it is preferable to use stable one such as diaphorase derived from *Bacillus stearothermophilus*. A typical concentration range of diaphorase in the analytical reagent is 0.01–1000 unit/ml, preferably 0.1–100 unit/mol. One unit of diaphorase activity is defined as the quantity of the enzyme which can reduce 1 μmol of tetrazolium dye per minute at pH 9.0 and 30° C.

Any kind of surfactant such as non-ionic and ionic surfactants can be used, however, it is preferable to use Triton (trade mark of Rohm & Haas Co.) series surfactants, more preferably Triton X-J100. A typical concentration range of the surfactant in the analytical reagent is greater than 0.001 w/v %, preferably 0.02–1 w/v %.

Now some examples of the present invention will be described hereunder for better understanding of the present invention. In the examples, the reagent in accordance with the present invention is applied to quantitative analysis of CEA. It should be noted, however, that the present invention is not limited thereto.

Firstly prepared is alkaline phosphatase labelled or linked anti-CEA antibody which is used in the examples shown hereunder.

PREPARATION OF ALKALINE PHOSPHATASE LABELLED ANTI-CEA ANTIBODY

To 2 mg of alkaline phosphatase (derived from calf intestine, purchased from Boehringer-Mannheim Yamanouchi K.K.), 3 mg of succinimidyl-4-(N-maleimidmethyl)- cyclohexane-1-carboxylate (purchased from Zieben Chemical Co.) was added, and the resultant mixture is subjected to reaction at pH 7.0, 30° C. for 10 minutes, thereby a maleimide group was introduced into a molecule of alkaline phosphatase. To the resultant solution, 1 mg of anti-carcinoembryonic antigen (hereinafter abbreviated as anti-CEA antibody) Fab' (prepared by digesting CEA antibody with pepsin, followed by reduction of the resultant digested antibody) was added at pH 6.0, thereby alkaline phosphatase labelled anti-CEA antibody having cross-linking between maleimide groups and thiol groups was prepared.

EXAMPLE 1

(1) Preparation of Analytical Reagent

Reagents (I) and (II) in accordance with the present invention were prepared in accordance with following compositions:

Reagents (I):

| | |
|---|---|
| diethanolamine buffer solution (pH 9.8) | 500 mM |
| $MgCl_2$ | 1 mM |
| NADP | 1 mM |
| EtOH | 100 mM |

Reagents (II):

| | |
|---|---|
| sodium phosphate buffer (pH 6.5) | 250 mM |
| INT | 0.5 mM |
| Triton X-100 | 0.02% |
| diaphorase (UNITIKA LTD.) | 1 unit/ml |
| ADH (UNITIKA LTD.) | 1 unit/ml |

As a Control 1, Reagents (I') and (II') were prepared in accordance with following compositions:

Reagents (I'):

| | |
|---|---|
| diethenolamine buffer solution (pH 9.8) | 500 mM |
| $MgCl_2$ | 1 mM |
| NADP | 1 mM |

Reagents (II'):

| | |
|---|---|
| sodium phosphate buffer (pH 6.5) | 250 mM |
| INT | 0.5 mM |
| Triton X-100 | 0.02% |
| EtOH | 100 mM |
| diaphorase (UNITIKA LTD.) | 1 unit/ml |
| ADH (UNITIKA LTD.) | 1 unit/ml |

(2) Method for Measurement

Fifty (50) μl aliquot of CEA (carcinoembryonic antigen) solution in different concentration of 0, 1.25, 2.5, 5.0, 10.0 and 20.0 ng/ml was poured into each well of a microtiter plate fixed with anti-CEA antibody, then 50 μl aliquot of alkaline phosphatase labelled anti-CEA antibody which was previously prepared was added to each well in a concentration of 1 μg/ml. The plate was placed static condition at room temperature for 2 hours to allow antigen-antibody reaction in the resultant mixture. After washing each well with 20 mM tris-HCl buffer (pH 7.2) containing 0.2% of Tween-20, 0.2% of bovine serum albumin and 0.15M sodium chloride, 50 μl aliquot of 0.5M diethanolamine (pH 9.8) containing 1 mM of NADP and 1 mM of $MgCl_2$ was added into each well, then incubated at room temperature for exactly 10 minutes. To the resultant reaction mixture in each well, 50 μl aliquot of Reagent (I) previously prepared was added. After 10 minutes incubation at room temperature, 100 μl aliquot of Reagent (II) previously prepared was added, then incubated at room temperature for 10 minutes, then the reaction was stopped by addition of 50 μl aliquot of 1N HCl to each well. Absorbance ($\Delta A_{490}$) of the resultant reaction mixture in each well was measured with microliter plate autoanalizer, Biomeck-1000 (Beckman). The same procedures was performed using Reagents (I') and (II') to thereby measure the absorbance of the final reaction mixture.

Furthermore, as to Reagents (II) and (II'), absorbance was measured with 10 days interval up to 50 days after preparation of the Reagents.

(3) Results

The results are shown in Table 1 and FIG. 1. It is apparent from the results that reagents of Example 1 and Control 1 have almost the same sensitivity in quantitative analysis of phosphatase which in turn enables quantitative analysis of CEA.

Figure 2:
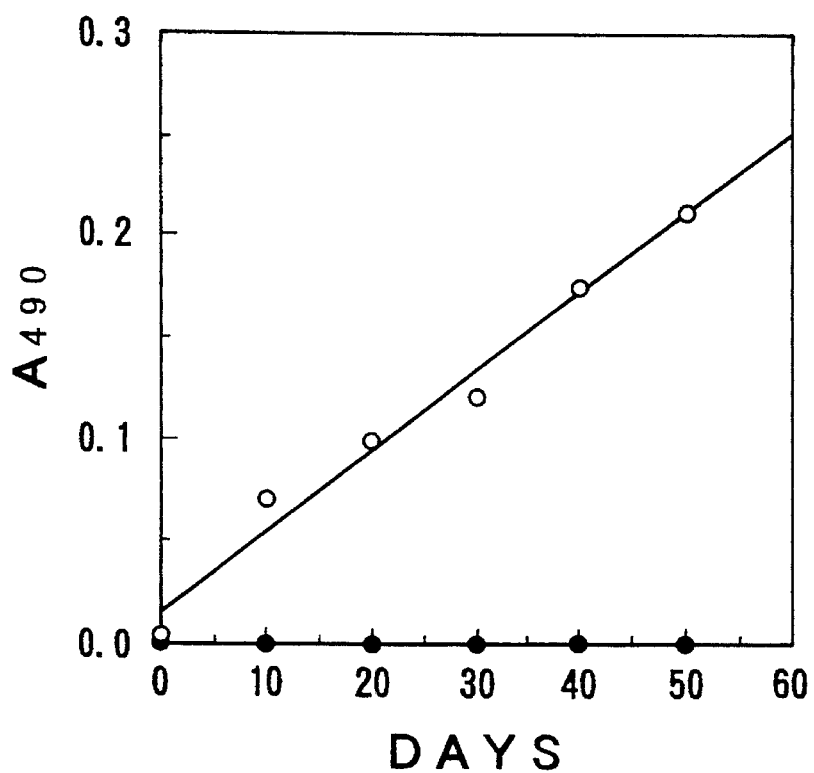
FIGS. 2, 4 and 6 show successive or periodical changes in absorbance ($A_{490}$) of Reagent II due to non-specific color-development.

As will be seen from the results of measurement of reagent blank in Reagents (II) and (I') shown in Table 2 and FIG. 2, reagent blank of Reagent (II') increased as the preservation period is prolonged, whereas, no reagent blank is observed in Reagent (II) in accordance with the present invention even after 50 days preservation, thereby excellent preservability and stability of the reagent of the present invention is demonstrated.

TABLE 1

| concentration of CEA (ng/ml) | absorbance ($A_{490}$) | |
|---|---|---|
| | Example 1 | Control 1 |
| 0 | 0.019 | 0.028 |
| 1.25 | 0.040 | 0.052 |
| 2.5 | 0.128 | 0.090 |
| 5.0 | 0.212 | 0.189 |
| 10.0 | 0.417 | 0.396 |
| 20.0 | 0.955 | 0.811 |

TABLE 2

| preservation (day) | absorbance ($A_{490}$) | |
|---|---|---|
| | Example 1 | Control 1 |
| 0 | 0.000 | 0.004 |
| 10 | 0.000 | 0.071 |
| 20 | 0.000 | 0.100 |
| 30 | 0.000 | 0.122 |
| 40 | 0.000 | 0.175 |
| 50 | 0.000 | 0.225 |

EXAMPLE 2

(1) Preparation of Analytical Reagent

Reagents (I) and (II) in accordance with the present invention were prepared in accordance with following compositions:

Reagents (I):

| | |
|---|---|
| diethanolamine buffer solution (pH 9.8) | 500 mM |
| $MgCl_2$ | 1 mM |
| NADP | 1 mM |
| diaphorase (UNITIKA LTD.) | 1 unit/ml |

Reagents (II):

-continued

| | |
|---|---|
| sodium phosphate buffer (pH 6.5) | 250 mM |
| INT | 0.5 mM |
| Triton X-100 | 0.02% |
| EtOH | 100 mM |
| ADH (UNITIKA LTD.) | 1 unit/ml |

As a Control 2, Reagents (I') and (II') were prepared in accordance with the following compositions:

| | |
|---|---|
| Reagents (I'): | |
| diethanolamine buffer solution (pH 9.8) | 500 mM |
| $MgCl_2$ | 1 mM |
| NADP | 1 mM |
| Reagents (II'): | |
| sodium phosphate buffer (pH 6.5) | 250 mM |
| INT | 0.5 mM |
| Triton X-100 | 0.02% |
| EtOH | 100 mM |
| diaphorase (UNITIKA LTD.) | 1 unit/ml |
| ADH (UNITIKA LTD.) | 1 unit/ml |

(2) Method for Measurement

In the same manner as in Example 1, concentration of CEA was measured using the reagent of the present invention and reagent blank of the Reagents (I) and (II') was tested.

(3) Results

Figure 3:
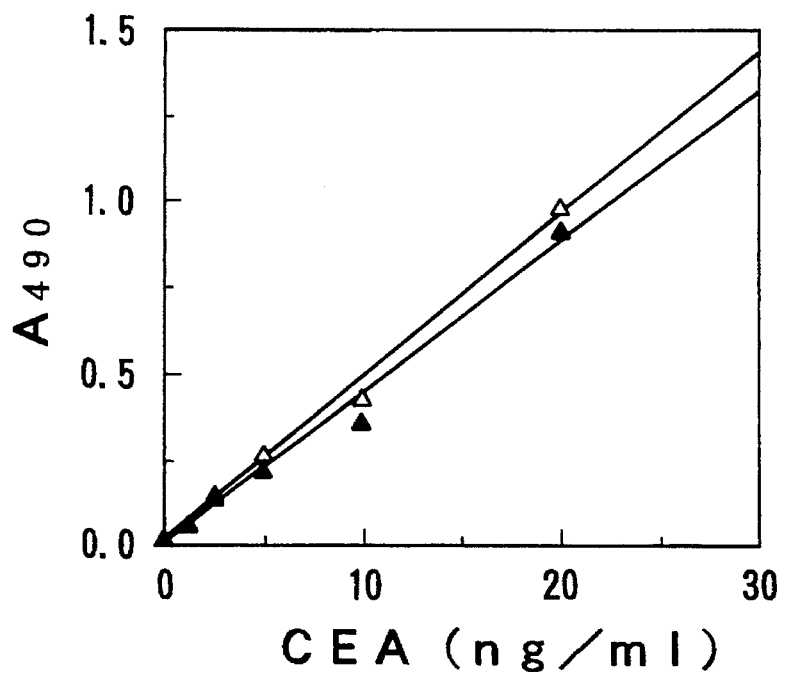

The results are shown in Table 3 and FIG. 3. It is apparent from the results that reagents of Example 2 and Control 2 have almost the same sensitivity in quantitative analysis of phosphatase which in turn enables to quantitative analysis of CEA.

Figure 4:
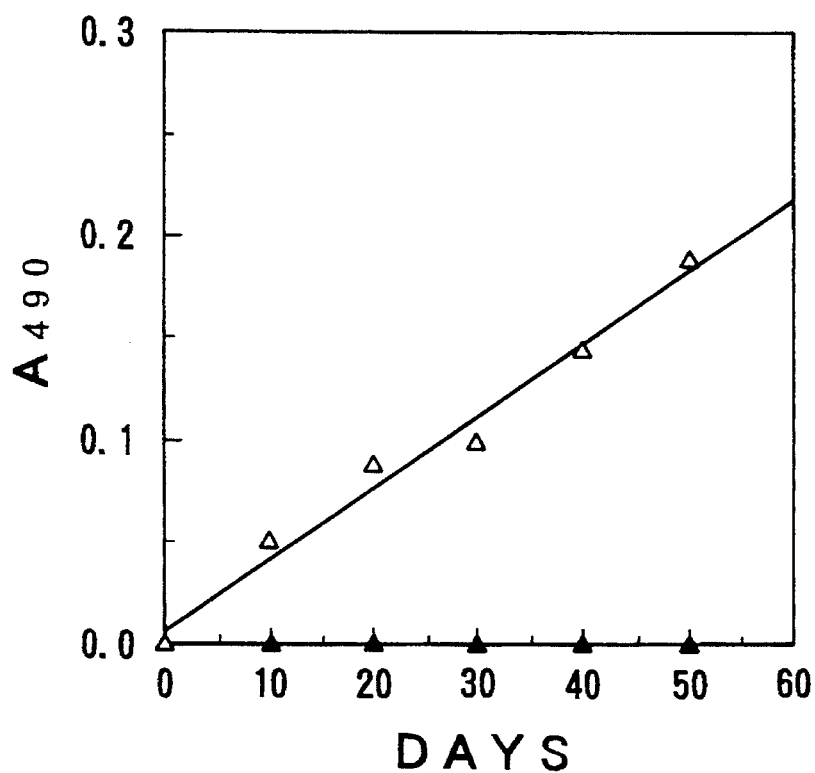

As will be seen from the results of measurement of reagent blank in Reagents (I) and (II') shown in Table 4 and FIG. 4, reagent blank of Reagent (II') increased as the preservation period is prolonged, whereas, no reagent blank is observed in Reagent (II) even after 50 days preservation, thereby excellent preservability and stability of the reagent of the present invention is demonstrated.

TABLE 3

| concentration | absorbance ($A_{490}$) | |
|---|---|---|
| of CEA (ng/ml) | Example 2 | Control 2 |
| 0 | 0.030 | 0.025 |
| 1.25 | 0.074 | 0.062 |
| 2.5 | 0.155 | 0.148 |
| 5.0 | 0.276 | 0.228 |
| 10.0 | 0.432 | 0.372 |
| 20.0 | 0.987 | 0.922 |

TABLE 4

| preservation | absorbance ($A_{490}$) | |
|---|---|---|
| (day) | Example 1 | Control 1 |
| 0 | 0.000 | 0.000 |
| 10 | 0.000 | 0.052 |
| 20 | 0.000 | 0.088 |
| 30 | 0.000 | 0.100 |
| 40 | 0.000 | 0.145 |
| 50 | 0.000 | 0.180 |

EXAMPLE 3

(1) Preparation of Analytical Reagent

Reagents (I) and (II) in accordance with the present invention were prepared in accordance with following compositions:

| | |
|---|---|
| Reagents (I): | |
| diethanolamine buffer solution (pH 9.8) | 500 mM |
| $MgCl_2$ | 1 mM |
| NADP | 1 mM |
| alanine | 50 mM |
| diaphorase (UNITIKA LTD.) | 1 unit/ml |
| Reagents (II): | |
| sodium phosphate buffer (pH 6.5) | 250 mM |
| INT | 0.5 mM |
| Triton X-100 | 0.02% |
| AlaDH (UNITAKA LTD.) | 1 unit/ml |

As a Control 3, Reagents (I') and (II') were prepared in accordance with following compositions:

| | |
|---|---|
| Reagents (I'): | |
| diethanolamine buffer solution (pH 9.8) | 500 mM |
| $MgCl_2$ | 1 mM |
| NADP | 1 mM |
| Reagents (II'): | |
| sodium phosphate buffer (pH 6.5) | 250 mM |
| INT | 0.5 mM |
| Triton X-100 | 0.02% |
| alanine | 50 mM |
| diaphorase (UNITIKA LTD.) | 1 unit/ml |
| AlaDH (UNITIKA LTD.) | 1 unit/ml |

(2) Method for Measurement

In the same manner as in Example 1, concentration of CEA was measured using the reagent of the present invention and reagent blank in the Reagent (I) and (II') was tested.

(3) Results

Figure 5:
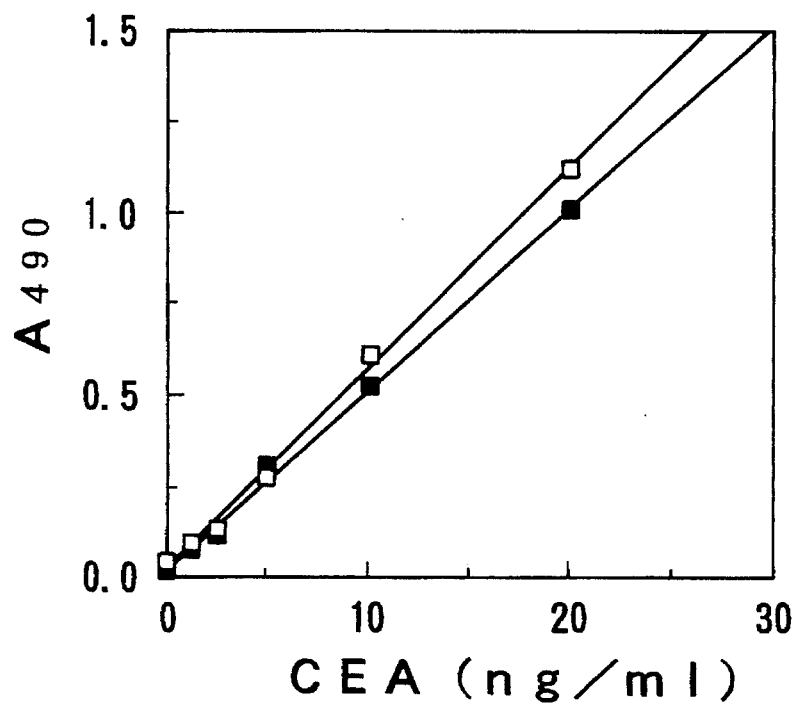

The results are shown in Table 5 and FIG. 5. It is apparent from the results that reagents of Example 3 and Control 3 have almost the same sensitivity in quantitative analysis of phosphatase which in turn enables quantitative analysis of CEA.

Figure 6:
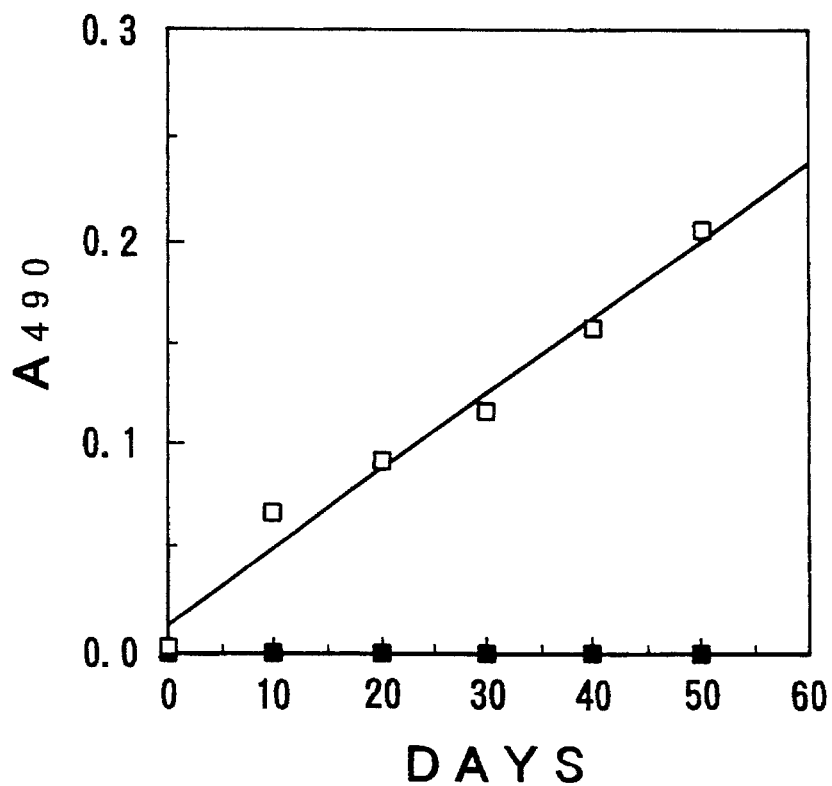

As will be seen from the results of measurement of reagent blank in Reagents (II) and (I') shown in Table 6 and FIG. 6, reagent blank of Reagent (II') increased as the preservation period is prolonged, whereas, no reagent blank is observed in Reagent (I) even after 50 days preservation, thereby excellent preservability and stability of the reagent of the present invention is demonstrated.

TABLE 5

| concentration of CEA (ng/ml) | absorbance ($A_{490}$) | |
| --- | --- | --- |
| | Example 3 | Control 3 |
| 0 | 0.040 | 0.018 |
| 1.25 | 0.091 | 0.072 |
| 2.5 | 0.135 | 0.115 |
| 5.0 | 0.279 | 0.303 |
| 10.0 | 0.613 | 0.522 |
| 20.0 | 1.114 | 1.010 |

TABLE 6

| preservation (day) | absorbance ($A_{490}$) | |
| --- | --- | --- |
| | Example 1 | Control 1 |
| 0 | 0.000 | 0.003 |
| 10 | 0.000 | 0.066 |
| 20 | 0.000 | 0.093 |
| 30 | 0.000 | 0.117 |
| 40 | 0.000 | 0.158 |
| 50 | 0.000 | 0.207 |

What is claimed is:

1. In a kit for measuring phosphatase in a sample, which kit comprises:

a first reagent participating in a catalytic reaction of phosphatase containing NADP or NADPH as a substrate for phosphatase which substrate is converted to NAD or NADH by the catalytic reaction of phosphatase, and a second reagent participating in a color-development amplification system containing (i) at least one of a first enzyme and a first substrate for the first enzyme, wherein the first enzyme, which is not a phosphatase, and first substrate, which is not NADP or NADPH, together are capable of reducing NAD generated by the first reagent to NADH, and (ii) at least one of a second enzyme and a second substrate for the second enzyme, wherein the second enzyme, which is not a phosphatase, and second substrate, which is not NADP or NADPH, together are capable of generating a color signal using NADH but not using NADP or NADPH, the improvement comprising incorporating into said first reagent at least one hydrogen donor compound selected from the enzymes and substrates of said second reagent, wherein said second reagent is thereby free of said hydrogen donor compound(s).

2. A kit according to claim 1, wherein one hydrogen donor compound is incorporated into said first reagent.

3. A kit according to claim 2, wherein two hydrogen donor compounds are incorporated into said first reagent.

4. A method for assaying a sample containing phosphatase comprising:

successively adding a first reagent and a second reagent as in claim 1 to a sample containing phosphatase and measuring the absorbance of a resulting reaction mixture.

* * * * *

UNITED STATES PATENT AND TRADEMARK OFFICE
CERTIFICATE OF CORRECTION

PATENT NO. : 5,529,906
DATED : June 25, 1996
INVENTOR(S) : Akiko Shimizu, et al

It is certified that error appears in the above-indentified patent and that said Letters Patent is hereby corrected as shown below:

On the cover page, delete "[73] Assignee: Mitsubishi Cable Industries, Ltd., Hyogo Prefecture, Japan".

Signed and Sealed this

Nineteenth Day of August, 1997

Attest:

BRUCE LEHMAN

Attesting Officer

Commissioner of Patents and Trademarks